United States Patent
Nebosky et al.

(10) Patent No.: US 9,724,203 B2
(45) Date of Patent: Aug. 8, 2017

(54) POROUS TISSUE INGROWTH STRUCTURE

(71) Applicant: SMed-TA/TD, LLC, Columbia City, IN (US)

(72) Inventors: Paul S. Nebosky, Fort Wayne, IN (US); Gregory C. Stalcup, Columbia City, IN (US); Troy D. Knapp, Alachua, FL (US)

(73) Assignee: SMed-TA/TD, LLC, Columbia, IN (US)

( * ) Notice: Subject to any disclaimer, the term of this patent is extended or adjusted under 35 U.S.C. 154(b) by 19 days.

(21) Appl. No.: 14/209,407

(22) Filed: Mar. 13, 2014

(65) Prior Publication Data

US 2014/0277461 A1 Sep. 18, 2014

Related U.S. Application Data

(60) Provisional application No. 61/789,723, filed on Mar. 15, 2013.

(51) Int. Cl.
*A61F 2/44* (2006.01)
*A61F 2/30* (2006.01)

(52) U.S. Cl.
CPC .......... *A61F 2/44* (2013.01); *A61F 2/442* (2013.01); *A61F 2/4455* (2013.01); *A61F 2002/30011* (2013.01); *A61F 2002/30013* (2013.01); *A61F 2002/30014* (2013.01); *A61F 2002/3079* (2013.01); *A61F 2002/3092* (2013.01);
(Continued)

(58) Field of Classification Search
CPC ...... A61L 27/56; A61L 2430/38; A61L 27/06; A61L 29/146; A61F 2/0077; A61F 2/3094; A61F 2310/00023; A61F 2002/0068; A61F 2002/30971; A61F 2250/0023;
(Continued)

(56) References Cited

U.S. PATENT DOCUMENTS 3,855,638 A 12/1974 Pilliar
3,867,728 A 2/1975 Stubstad et al.
(Continued)

FOREIGN PATENT DOCUMENTS

EP 0 621 018 A1 7/1993
WO 03/026714 A1 4/2003

OTHER PUBLICATIONS

Notification of Transmittal of the International Search Report and the Written Opinion of the International Searching Authority, or the Declaration dated Aug. 6, 2014 for International Application No. PCT/US2014/027796 (14 pages).
(Continued)

*Primary Examiner* — Eduardo C Robert
*Assistant Examiner* — Tara R Carter
(74) *Attorney, Agent, or Firm* — Taylor IP, P.C.

(57) ABSTRACT

A three-dimensional scaffold for a medical implant includes a plurality of layers bonded to each other. Each layer has a top surface and a bottom surface and a plurality of pores extending from the top surface to the bottom surface. Each layer has a first pore pattern of the pores at the top surface and a different, second pore pattern at the bottom surface. Adjacent surfaces of at least three adjacent layers have a substantially identical pore pattern aligning to interconnect the pores of the at least three adjacent layers to form a continuous porosity through the at least three adjacent said layers.

21 Claims, 6 Drawing Sheets

(52) U.S. Cl.
CPC .............. *A61F 2002/30784* (2013.01); *A61F 2002/30807* (2013.01); *A61F 2002/30813* (2013.01); *A61F 2002/30841* (2013.01); *A61F 2002/30915* (2013.01); *A61F 2002/30971* (2013.01); *Y10T 156/10* (2015.01)

(58) Field of Classification Search
CPC ............ A61F 2/4455; A61F 2220/0025; A61F 2220/0033; A61F 2230/0063
USPC ........ 606/246–249; 623/23.74, 17.11–17.16; 264/273, 413, 414
See application file for complete search history.

(56) References Cited

U.S. PATENT DOCUMENTS

| | | |
|---|---|---|
| 4,011,602 A | 3/1977 | Rybicki et al. |
| 4,222,128 A | 9/1980 | Tomonaga et al. |
| 4,608,052 A | 8/1986 | Van Kampen et al. |
| 4,737,411 A | 4/1988 | Graves, Jr. et al. |
| 4,769,041 A | 9/1988 | Morscher |
| 4,846,834 A | 7/1989 | von Recum et al. |
| 4,976,738 A | 12/1990 | Frey et al. |
| 5,030,233 A | 7/1991 | Ducheyne |
| 5,104,410 A | 4/1992 | Chowdhary |
| 5,204,055 A | 4/1993 | Sachs et al. |
| 5,219,363 A | 6/1993 | Crowninshield et al. |
| 5,282,861 A | 2/1994 | Kaplan |
| 5,348,788 A | 9/1994 | White |
| 5,380,328 A | 1/1995 | Morgan |
| 5,490,962 A | 2/1996 | Cima et al. |
| 5,496,372 A | 3/1996 | Hamamoto et al. |
| 5,518,680 A | 5/1996 | Cima et al. |
| 5,571,187 A | 11/1996 | Devanathan |
| 5,637,175 A | 6/1997 | Feygin et al. |
| 5,730,817 A | 3/1998 | Feygin et al. |
| 5,732,469 A | 3/1998 | Hamamoto et al. |
| 5,807,406 A | 9/1998 | Brauker et al. |
| 5,824,054 A | 10/1998 | Khosravi et al. |
| 5,869,170 A | 2/1999 | Cima et al. |
| 5,876,550 A | 3/1999 | Feygin et al. |
| 6,010,336 A | 1/2000 | Shimotoso et al. |
| 6,136,029 A | 10/2000 | Johnson et al. |
| 6,139,574 A | 10/2000 | Vacanti et al. |
| 6,143,035 A | 11/2000 | McDowell |
| 6,143,293 A | 11/2000 | Weiss et al. |
| 6,176,874 B1 | 1/2001 | Vacanti et al. |
| 6,261,320 B1 | 7/2001 | Tam et al. |
| 6,306,424 B1 | 10/2001 | Vyakarnam et al. |
| 6,328,765 B1 | 12/2001 | Hardwick et al. |
| 6,333,029 B1 | 12/2001 | Vyakarnam et al. |
| 6,337,198 B1 | 1/2002 | Levene et al. |
| 6,365,149 B2 | 4/2002 | Vyakarnam et al. |
| 6,409,764 B1 | 6/2002 | White et al. |
| 6,423,252 B1 | 7/2002 | Chun et al. |
| 6,440,734 B1 | 8/2002 | Pykett et al. |
| 6,461,385 B1 | 10/2002 | Gayer et al. |
| 6,471,993 B1 | 10/2002 | Shastri et al. |
| 6,488,701 B1 | 12/2002 | Nolting et al. |
| 6,514,514 B1 | 2/2003 | Atkinson et al. |
| 6,520,997 B1 | 2/2003 | Pekkarinen et al. |
| 6,526,984 B1 | 3/2003 | Nilsson et al. |
| 6,527,810 B2 | 3/2003 | Johnson et al. |
| 6,530,958 B1 | 3/2003 | Cima et al. |
| 6,533,818 B1 | 3/2003 | Weber et al. |
| 6,534,084 B1 | 3/2003 | Vyakarnam et al. |
| 6,544,472 B1 | 4/2003 | Compton et al. |
| 6,554,857 B1 | 4/2003 | Zilla et al. |
| 6,571,130 B1 | 5/2003 | Ljungstrom et al. |
| 6,599,322 B1 | 7/2003 | Amrich et al. |
| 6,626,950 B2 | 9/2003 | Brown et al. |
| 6,673,108 B2 | 1/2004 | Zilla et al. |
| 6,712,850 B2 | 3/2004 | Vyakarnam et al. |
| 6,783,546 B2 | 8/2004 | Zucherman et al. |
| 6,852,272 B2 | 2/2005 | Artz et al. |
| 6,881,413 B1 | 4/2005 | Bartholeyns |
| 6,893,465 B2 | 5/2005 | Huang |
| 6,993,406 B1 | 1/2006 | Cesarano, III et al. |
| 7,018,418 B2 | 3/2006 | Amrich et al. |
| 7,052,710 B2 | 5/2006 | Giordano et al. |
| 7,087,200 B2 | 8/2006 | Taboas et al. |
| 7,108,828 B2 | 9/2006 | Lefebvre et al. |
| 7,174,282 B2 | 2/2007 | Hollister et al. |
| 7,189,409 B2 | 3/2007 | Pirhonen et al. |
| 7,208,222 B2 * | 4/2007 | Rolfe et al. ................ 428/304.4 |
| 7,250,060 B2 | 7/2007 | Trieu |
| 7,384,786 B2 | 6/2008 | Freyman et al. |
| 7,537,617 B2 | 5/2009 | Bindsell et al. |
| 7,537,664 B2 | 5/2009 | O'Neill et al. |
| 7,632,228 B2 | 12/2009 | Brauker et al. |
| 7,666,230 B2 | 2/2010 | Orban et al. |
| 7,674,426 B2 | 3/2010 | Grohowski, Jr. |
| 7,674,477 B1 | 3/2010 | Schmid et al. |
| 8,071,007 B1 | 12/2011 | Teoh et al. |
| 2002/0072798 A1 | 6/2002 | Riesle et al. |
| 2003/0130718 A1 | 7/2003 | Palmas et al. |
| 2003/0171820 A1 | 9/2003 | Wilshaw et al. |
| 2004/0191292 A1 | 9/2004 | Chou |
| 2005/0085893 A1 | 4/2005 | Roy |
| 2005/0100578 A1 | 5/2005 | Schmid et al. |
| 2005/0112397 A1 | 5/2005 | Rolfe et al. |
| 2005/0177247 A1 | 8/2005 | Canham et al. |
| 2005/0228503 A1 | 10/2005 | Gundolf |
| 2005/0246032 A1 | 11/2005 | Bokros et al. |
| 2006/0178744 A1 | 8/2006 | de Villiers et al. |
| 2006/0282166 A1 | 12/2006 | Molz et al. |
| 2007/0038299 A1 | 2/2007 | Stone et al. |
| 2007/0105222 A1 | 5/2007 | Wolfinbarger et al. |
| 2007/0116734 A1 | 5/2007 | Akash |
| 2007/0185585 A1 | 8/2007 | Bracy et al. |
| 2007/0190880 A1 | 8/2007 | Dubrow et al. |
| 2007/0191963 A1 | 8/2007 | Winterbottom et al. |
| 2007/0196419 A1 | 8/2007 | Teller et al. |
| 2007/0203584 A1 | 8/2007 | Bandyopadhyay et al. |
| 2010/0042167 A1 | 2/2010 | Nebosky et al. |
| 2010/0042215 A1 | 2/2010 | Stalcup et al. |
| 2010/0042218 A1 | 2/2010 | Nebosky et al. |
| 2010/0161061 A1 | 6/2010 | Hunt |
| 2010/0190254 A1 | 7/2010 | Chian et al. |
| 2010/0291176 A1 | 11/2010 | Chian et al. |
| 2010/0291286 A1 | 11/2010 | O'Neill et al. |
| 2011/0064784 A1 | 3/2011 | Mullens et al. |
| 2011/0153028 A1 | 6/2011 | Albertorio |

OTHER PUBLICATIONS

Notification of Transmittal of the International Search Report and the Written Opinion of the International Searching Authority, or the Declaration dated Jul. 24, 2014 for International Application No. PCT/US2014/024424 (17 pages).

Bryan, R.S. et al. "The Effect of Polyvinyl-Formal (Ivalon) Sponge on Cortical Bone Healing." Proceedings of the Staff Meetings of the Mayo Clinic vol. 33 (1958): 453-457 (3 pages).

Galante, J. et al. "Sintered Fiber Metal Composites as a Basis for Attachment of Implants to Bone." Journal of Bone and Joint Surgery Am 53 (1971):101-114 (15 pages).

Bobyn, J.D., Pilliar, R.M., Cameron, H.U., and Weatherly, G.C. "The Optimum Pore Size for Fixation of Porous-Surfaced Metal Implants by the Ingrowth of Bone." Clinical Orthopedics and Related Research. 150 (1980): 263-270 (8 pages).

Bobyn, J.D., Stackpool, G.J., Hacking, S.A., Tanzer, M., and Krygier, J.J. "Characteristics of Bone Ingrowth and Interface Mechanics of a New Porous Tantalum Biomaterial." The Journal of Bone & Joint Surgery (Br) vol. 81-B (1999): 907-914 (8 pages).

Hulbert, S.F., Young, F.A., Mathews, R.S., Klawitter, J.J., Talbert, C.D., Stelling, F.H. "Potential of Ceramic Materials as Permanently Implantable Skeletal Prostheses." Journal of Biomedical Materials Research. 4 (1970): 433-456 (24 pages).

Levine, B. "A New Era in Porous Metals: Applications in Orthopaedics." Advanced Engineering Materials. 10 (2008): 788-792 (5 pages).

(56) References Cited

OTHER PUBLICATIONS

"Biofoam Technical Monograph", Cancellous Titanium Matrix, Fixation with Bite, Wright Medical, 2009.
International Preliminary Report on Patentability and the Written Opinion dated Sep. 15, 2015 for International Application No. PCT/US2014/027796 (11 pages).
Extended European Search Report dated Aug. 25, 2016 for European Patent Application No. 14 76 3785 (8 pages).

* cited by examiner

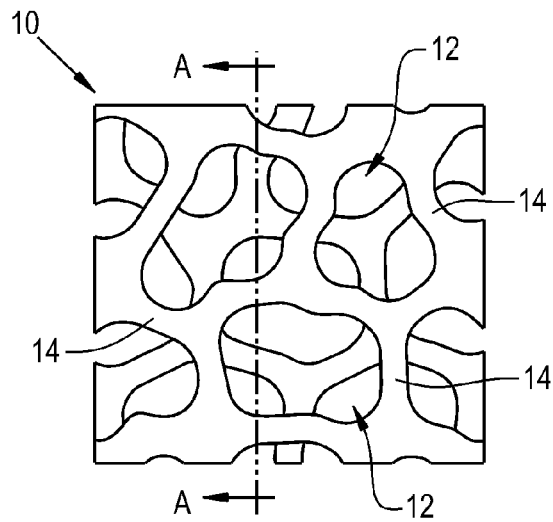
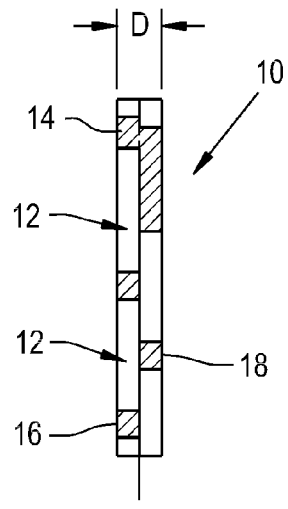
Fig. 1
Fig. 2
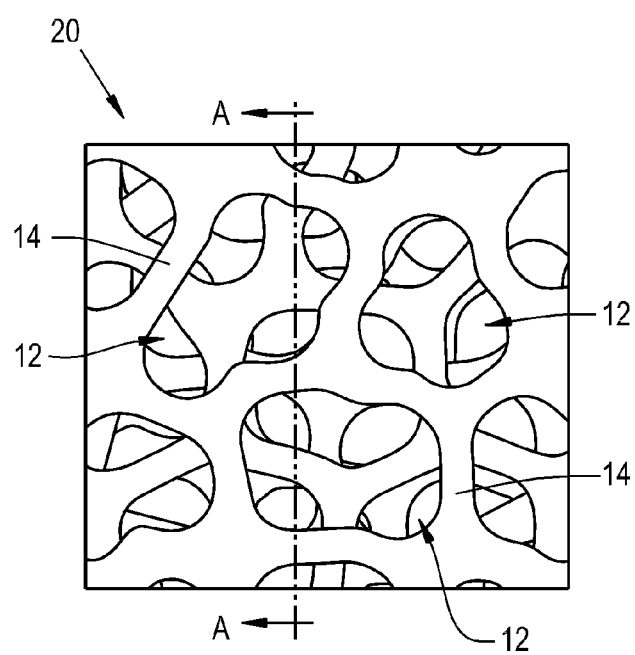
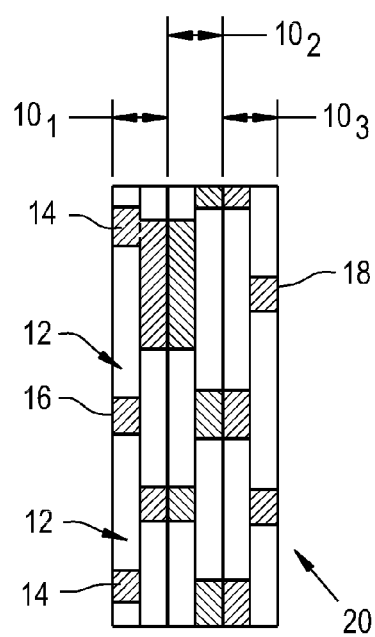
Fig. 3
Fig. 4

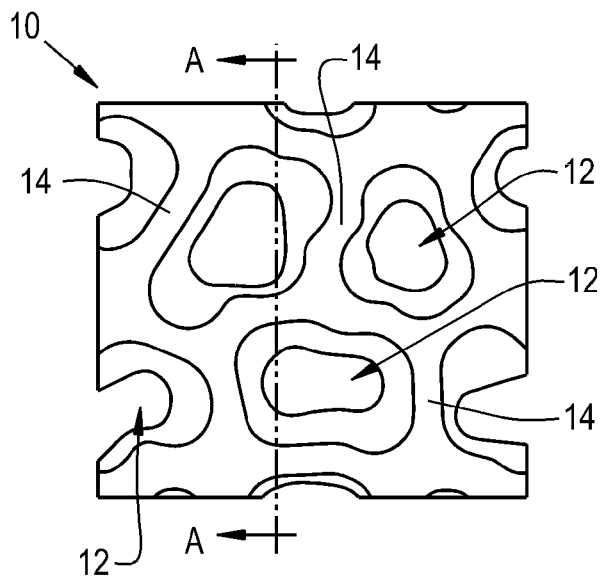
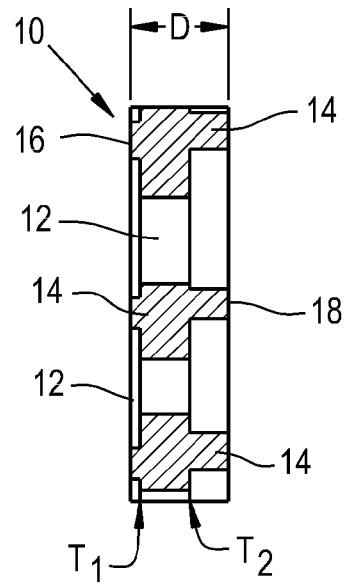
Fig. 5     Fig. 6
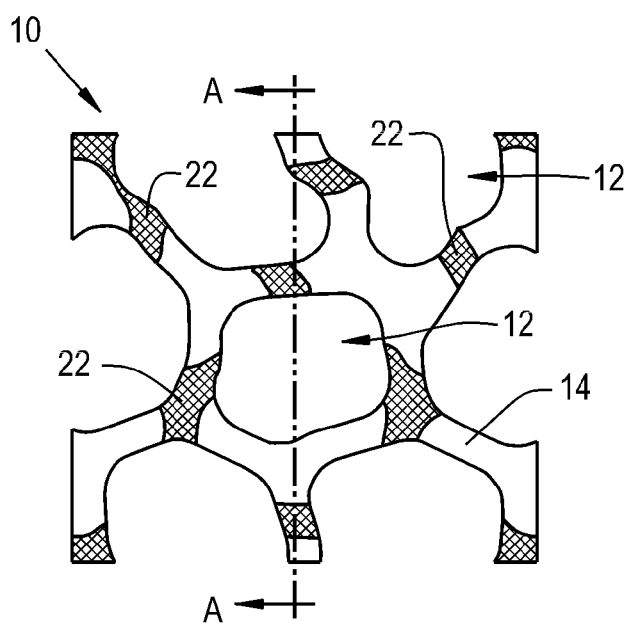
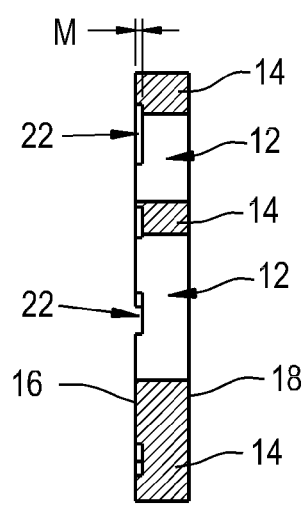
Fig. 7     Fig. 8

POROUS TISSUE INGROWTH STRUCTURE

CROSS REFERENCE TO RELATED APPLICATIONS

This is a non-provisional application based upon U.S. Provisional Patent Application Ser. No. 61/789,723, entitled "POROUS TISSUE INGROWTH STRUCTURE", filed Mar. 15, 2013, which is incorporated herein by reference.

BACKGROUND OF THE INVENTION

1. Field of the Invention

The present invention relates to medical implants, and, more particularly, to medical implants having a bone and tissue ingrowth structure, and to a method of manufacturing the medical implants.

2. Description of the Related Art

Implant fixation via bone and tissue integration into a porous scaffold has been in development since the 1950s, when polyvinyl sponges were implanted into canines (Bryan, R. S., et al., "The Effect of Polyvinyl-Formal (Ivalon) Sponge on Cortical Bone Healing." *Proceedings of the Staff Meetings, Mayo Clinic,* 33 (1958): 453-457). The early 1970s saw the development of sintered beads and titanium fiber metal, which are still in use in orthopaedic implants today. (Galante, J., Et al., "Sintered Fiber Metal Composites as a Basis for Attachment of Implants to Bone." *Journal of Bone and Joint Surgery Am,* 563 (1971): 101-114).

In the Mid 1990s, a design was developed for porous scaffolds for tissue ingrowth. For example, U.S. Pat. No. 5,732,469 discloses a prosthesis for the replacement of hard tissues of human bones and joints formed by a porous lamination component of thin, metal layers, each of which have a different pore pattern. Further, U.S. Pat. No. 6,010,336 discloses a living body-supporting member having a porous surface layer formed of ceramic material. However, the scaffolds known in the art which are constructed to encourage bone ingrowth have reduced strength due to the low contact area between adjacent layers. More specifically, the weak points in laminate scaffolds known in the art are in the resulting layer interfaces between individual layers, especially in shear parallel to these interfaces. Accordingly, if the scaffold struts are too thin, the scaffold will not satisfy the necessary strength. Additionally, implants formed from the laminate of thin metal layers are costly to produce, since the scaffold's strength must be bolstered by increased minimum thickness of the layers.

What is needed in the art is a medical implant which has an improved strength, particularly shear strength in planes parallel to individual layers, and which may be manufactured in a cost-effective way.

SUMMARY OF THE INVENTION

The present invention provides a medical implant, and, more particularly, a medical implant having a bone and tissue ingrowth structure, as well as a method of manufacturing the medical implant.

The present invention in one form is directed to a three-dimensional scaffold for a medical implant including a plurality of layers bonded to each other, each layer having a top surface and a bottom surface. Each of the layers have a plurality of pores extending from the top surface to the bottom surface. Further, each layer has a first pore pattern of the plurality of pores at the top surface and a different, second pore pattern at the bottom surface. Adjacent surfaces of at least three adjacent of the layers have a substantially identical pore pattern aligning to interconnect the pores of the at least three adjacent layers to form a continuous porosity through the at least three adjacent said layers.

The invention in another form is directed to a medical implant including a main body and at least one three-dimensional scaffold coupled with the main body. The at least one scaffold includes a plurality of layers bonded to each other, each layer having a top surface and a bottom surface and a plurality of pores extending from the top surface to the bottom surface. Each layer has a first pore pattern of the pores at the top surface and a different, second pore pattern at the bottom surface. Adjacent surfaces of at least three adjacent layers have a substantially identical pore pattern aligning to interconnect the pores of the at least three layers and form a continuous porosity through the at least three adjacent said layers.

The present invention further provides a method of manufacturing a scaffold for a medical implant including the provision of a plurality of layers of a biocompatible material having a top surface and a bottom surface. A plurality of pores are created in the plurality of layers of biocompatible material such that each layer has a plurality of pores extending from the top surface to the bottom surface. A first pore pattern of the pores at the top surface of each of said layers is different than a second pore pattern at the bottom surface of each of the layers. The layers are bonded together such that adjacent surfaces of at least three adjacent layers have a substantially identical pore pattern aligning to interconnect the pores of the at least three adjacent layers, forming a continuous porosity through the at least three adjacent layers.

An advantage of the present invention is that, due to the alignment of the pore patterns, the strength of the produced three-dimensional scaffold is increased, especially shear strength in planes parallel to individual layers.

Another advantage is provided by the present invention since the alignment of the pore patterns further requires the alignment of the struts surrounding the pores at the adjacent surfaces of adjacent layers, more cost effective manufacturing is possible through reduction of the minimum strut thickness required. Additionally, the configuration and positioning of the layers forming the 3-dimensional scaffold according to the present invention provide for improved aesthetics of the resulting scaffold.

BRIEF DESCRIPTION OF THE DRAWINGS

The above-mentioned and other features and advantages of this invention, and the manner of attaining them, will become more apparent and the invention will be better understood by reference to the following description of an embodiments of the invention taken in conjunction with the accompanying drawings, wherein:

FIG. 1 is a top view of a single layer of a scaffold according to the present invention;

FIG. 2 is a sectional view of the single layer of a scaffold along the A-A line, illustrated in FIG. 1;

FIG. 3 is a top view of a scaffold for a medical implant according to the present invention;

FIG. 4 is a sectional view of the scaffold of FIG. 3 along the A-A line;

FIG. 5 is a top view of a layer of a scaffold according to the present invention;

FIG. 6 is a sectional view of the layer of scaffold of FIG. 5 along the A-A line;

FIG. 7 is a top view an additional embodiment of a layer of a scaffold according to the present invention;

FIG. 8 is a sectional view of the layer of scaffold of FIG. 7 along the A-A line;

Corresponding reference characters indicate corresponding parts throughout the several views. The exemplifications set out herein illustrate embodiments of the invention and such exemplifications are not to be construed as limiting the scope of the invention in any manner.

DETAILED DESCRIPTION OF THE INVENTION

Figure 9:
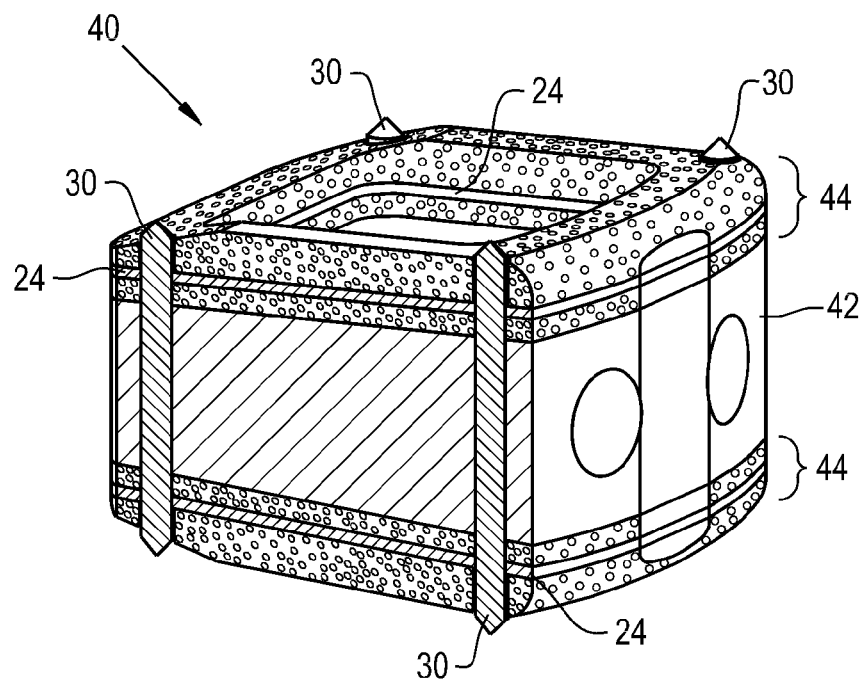
FIG. 9 is a sectioned perspective view of a medical implant according to the present invention.

Referring now to the drawings, and more particularly to FIGS. 1 and 2, there is shown a single layer 10 of a three-dimensional scaffold for a medical implant according to the present invention. Single layer 10 includes a plurality of pores or through-holes 12 defined by a plurality of struts 14. The geometries of the pores 12 vary through a thickness D of each layer 10. Any layer thickness D can be used, for example layer thickness D may be in a range of, for example, between approximately 0.0001 inch (in) and 10 in, for example 0.0001 to 0.040 in, or 0.020 to 0.040 in. Further, struts 14 are defined as bars of material extending between and defining pores 12. Each layer 10 has a first pore pattern at a top surface 16 and different, second pore pattern at an opposing, bottom surface 18. Transition from the first pore pattern to the second pore pattern takes place at a location or transition point T, where T is defined by the equation T=A*D, with T being a defined distance from the top surface 16 of layer 10 toward the bottom surface 18, and A representing a fraction of the thickness of layer 10. A is in a range of 0<A<1, for example, in a range between approximately 0.05 and 0.95, for example between approximately 0.35 and 0.65.

Layers 10 are formed of biocompatible materials including metals, polymeric material and zirconia. Suitable metals include titanium and titanium alloys, tantalum and tantalum alloys, cobalt chrome alloys, stainless steel and alumina. Exemplary polymeric materials include polyaryletherketone (PAEK) polymers, such as polyetheretherketone (PEEK), polyetherketone (PEK), Polyetherketoneketone (PEKK), polyetherketone etherketone ketone (PEKEKK), polyethylene, polyurethane.

Referring now to FIGS. 3 and 4, there is shown a three-dimensional scaffold 20, which resembles a rigid sponge, for a medical implant according to the present invention, including a plurality of the layers 10 of FIG. 1 bonded to each other, one on top of another. Three-dimensional scaffold 20 includes at least three layers 10, for example 4, 5, 6 or more layers. According to the present invention at least three of layers 10 ($10_1$, $10_2$, $10_3$) have a first pore pattern at top surface 16 and a second, different pattern at bottom surface 18 and are positioned such that the pore patterns of respective adjacent surfaces 16, 18 of at least three adjacent layers are substantially identical, for example identical, and align with one another over the course of at the least three adjacent layers, for example 4, 5, or 6 or more adjacent layers. Thus, pores 12 of each of the at least three layers 10 are interconnected with one another to form continuous porosity or path through the at least three layers 10. Due to the specified construct, scaffold 20 is configured for facilitation of bone or tissue ingrowth.

Accordingly, an exemplary three-dimensional scaffold 20 according to the present invention may have the following structure:

On layer I, the pore pattern on the top surface is Pore Pattern A, and the pore pattern on the bottom surface is Pore Pattern B.

On layer II, the pore pattern on the top surface is Pore Pattern B, and the pore pattern on the bottom surface is Pore Pattern C.

On layer III, the pore pattern on the top surface is Pore Pattern C, and the pore pattern on the bottom surface is Pore Pattern D.

Although the example above includes four pore patterns, it is feasible to have as few as two different pore patterns. It is also feasible to have more pore patterns, dependent upon the number of layers 10 forming scaffold 20. Further, although the example set forth above includes only three layers 10, it is also feasible to include more than three layers in scaffold 20. Any additional layers forming scaffold 20 may or may not be porous and, if they are porous, may or may have a pore pattern which matches up with the pore pattern of the adjacent surface of adjacent layer(s). For example, it is possible to have an additional, fourth layer having the same pore pattern as the adjacent surface, but not be aligned with the pore pattern of the adjacent surface. Alternatively, the pore pattern of an additional, fourth layer may have a different pore pattern than the adjacent surface(s) of the adjacent layer(s).

Since, the pore pattern of adjacent surfaces of adjacent layers mate up substantially identical to each other through at least three adjacent layers 10 of an inventive scaffold 20, the contact area of the struts 14 is high at the adjacent surfaces of these adjacent layers. The weak points of the scaffold 20 are thereby moved to the inside of the individual layers 10 rather than the interfaces between layers 10 and the tolerance of the strut width can be increased. In other words, the strut width can be decreased, thereby maximizing the potential porosity and pore interconnectivity, while maintaining or improving the strength of the strut 14, and the thereby formed scaffold 20.

Referring now to FIG. 5, there is shown an embodiment of a layer 10 for a scaffold 20 which includes pores 12 having at least two different geometries as they progress from top surface 16 to bottom surface 18 of layer 10. Pores 12 of layer 10 for scaffold 20 according to the present invention may, however, include any number of different geometries, for example 2, 3, 4 or more different geometries as the pores 12 progress from top surface 16 to bottom surface 18.

Referring now to FIG. 6, there is shown a sectional view of layer 10 along line A-A of FIG. 5 having more than two different pore patterns through thickness D of layer 10, which extends between top surface 16 and bottom surface 18. Layer 10 thus includes two transition points $T_1$ and $T_2$, thereby including a first pore pattern at top surface 16, a second pore pattern which initiates at first transition point $T_1$, and a third pore pattern which initiates at second transition point $T_2$ and extends to bottom surface 18. In other words, in the example shown in FIG. 6, the first pore pattern extends between top surface 16 and first transition point $T_1$, the second pore pattern extends between first transition point $T_1$ and second transition point $T_2$, and the third pore pattern extends between second transition point $T_2$ and bottom surface 18. In this example, first transition point $T_1$ is determined by the equation $T_1=A*D$, wherein A is a fraction between 0 and 1 and D is the thickness of layer 10, which extends between top surface 16 and bottom surface 18. Further, second transition point $T_2$ is determined by the equation $T_2=B*D$, wherein B is a fraction between 0 and 1 of layer thickness D. In this example, the values for A and B are such that $0<A<B<1$.

According to a further embodiment of the scaffold according to the present invention, there may be provided interlocking features 22 that increase strength, most notably shear strength. For example, interlocking features 22 may be configured to allow adjacent layers to nest together. Once they are stacked, they may then be bonded together to form three-dimensional scaffold 20. For example, referring now to FIGS. 7 and 8, there is shown an embodiment of a surface 16 or 18 of layer 10 according to the present invention where interlocking features 22 are in the form of a plurality of undercuts 22 formed in surface 16 or 18 of layer 10. FIG. 8 is a sectional view along line A-A of FIG. 7, which illustrates an exemplary undercut 22 according to the present invention in relation to struts 14 and pores 12 of layer 10. Undercuts 22 have a depth M relative to the thickness D of layer 10, wherein depth M is a fraction of the thickness D, and thus $M=C*D$, with C being a predetermined fraction of D, and C being between 0 and 1. Undercuts 22 can be formed on one or both sides of each layer 10 of scaffold 20. Further, corresponding projections (not shown) on another layer may be used to seat another layer within undercuts 22 on an adjacent layer 10. If projections are not used, then struts 14 of an adjacent layer 10 can seat within corresponding undercuts 22. These undercuts 22 thus are interlocking features 22 which lock one layer 10 together with an adjacent layer 10.

Figure 11:
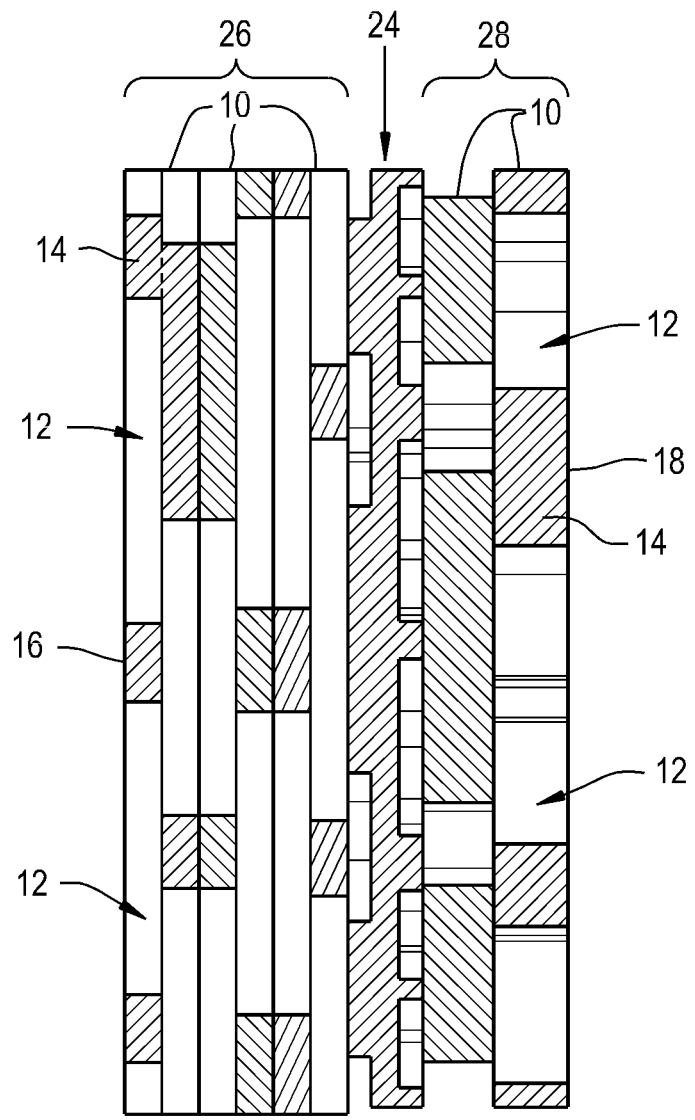
FIG. 11 is a sectioned side view of an additional embodiment of a scaffold according to the present invention.
Figure 12:
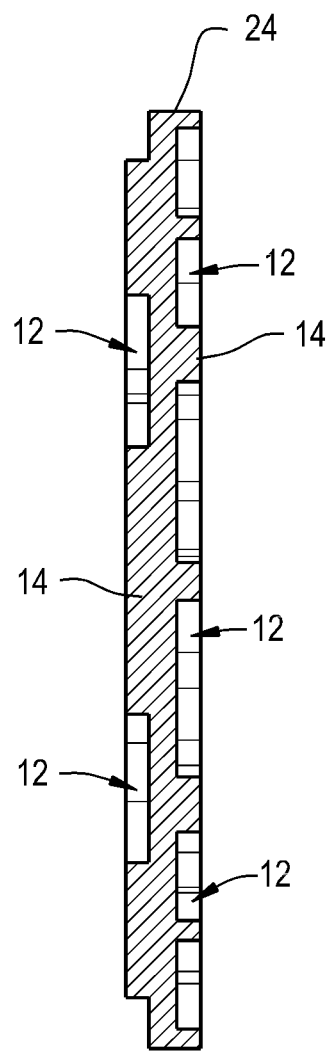
FIG. 12 is a sectioned side view of the stiffening layer of the scaffold according to claim 11.

Referring now to FIGS. 11 and 12, scaffold 20 may further include at least one stiffening layer 24 in the form of a rigid, solid material. Stiffening layer 24 may be positioned on an outside surface, for example a bottom surface 18, of layers 10 solely for purposes of providing additional strength and support to scaffold 20, and/or may be positioned to separate scaffold 20 into multiple regions. Stiffening layer 24 provides added strength and rigidity, for example, when a medical implant is formed including the scaffolding and, for example, an additional solid body. In such a case, stiffening layer 24 provides added rigidity during, for example injection molding, thereby helping to resist deformation during manufacture while injection forces are high. Additionally, stiffening layer 24 prevents the flow of material from one region through to another region on an opposite side of stiffening layer 24.

Additionally, at least one stiffening layer 24 may be connected to another body, for example a solid body or another scaffold 20 according to the present invention with at least one alignment and/or fixation device 30, for example fixation pins, spikes, stakes or screws. For example, fixation pins 30 can be press-fit into stiffening layer 24 to hold the components in place for purposes of injection molding of an additional body to form a desired implant. Further, stiffening layer 24 advantageously provides an indicator for implant orientation when viewed via MRI, CT, or X-ray. Stiffening layer 24 may be formed of any biocompatible metal or polymer/plastic, such as, but not limited to, titanium, tantalum, or PEEK.

For exemplary purposes, scaffold 20 may include stiffening layer 24 which separates a porous bone ingrowth region 26 formed from layers 10 and a porous polymer retention or poly retention region 28, also formed from layers 10. Stiffening layer 24 is, for example, formed from a solid, non-porous layer, thereby providing a fluid barrier between bone ingrowth region 26 and poly retention region 28. Advantageously, bone ingrowth region 26 provides a roughened surface for initial implant stability, and later, with bone ingrowth, long term stability, while poly retention region 28 provides a series of interconnected pores 12 and channels for polymeric material, such as PEEK, to flow therethrough for purposes of forming an interlocking anchor, locking the PEEK to the scaffold material.

A further embodiment of stiffening layer 24 includes pores 25 which do not extend through the entire thickness of layer 24, thereby preventing fluid flow through from a layer 10 on one side of stiffening layer 24 to another layer 10 on an opposing side of stiffening layer 24. Stiffening layer 24 may further include a pore pattern on each side, which does not extend through an entire thickness of stiffening layer 24 such that there is no fluid flow path from one side of layer 24 through to the other side of layer 24, as is illustrated in FIGS. 11 and 12. Stiffening layer 24 can be manufactured, for example by stamping, photochemical etching, laser etching, machining, micro-milling, or electron beam machining, to name a few.

Figure 13:
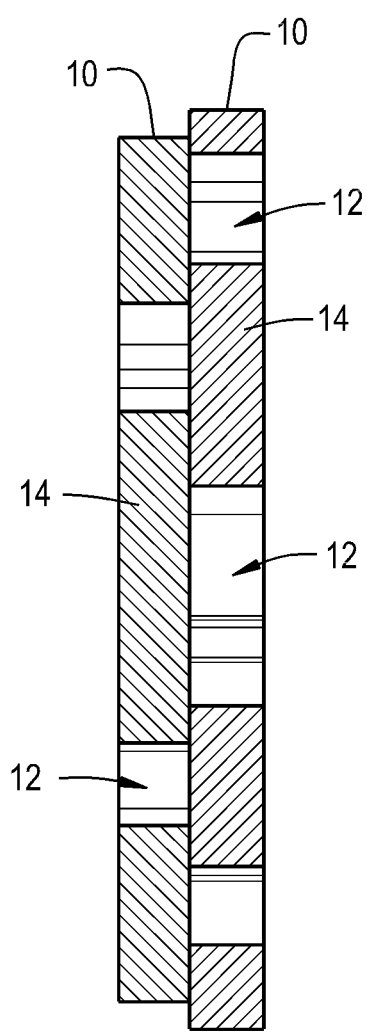
FIG. 13 is a sectioned side view of a further embodiment of a barrier layer for a scaffold according to the present invention.

Alternatively, according to another embodiment of the scaffold 20 according to the present invention, there may be included two adjacent layers 10 having adjacent surfaces which have pore patterns formed such that there is no interconnectivity of pores 12 of the surfaces of the adjacent layers, as illustrated at FIG. 13. Thus, although the pores can go all the way through each respective layer, there is no fluid flow path between the respective layers. Thus, solid areas of one layer, in the form of struts, block the path formed by the pores in the adjacent layer, thereby forming a fluid barrier. According to this embodiment of the present invention, a separate stiffening layer 24 is not necessary since the two adjacent layers 10 are aligned such that there is no fluid flow path between the pores of one layer 10 to the adjacent layer 10, thereby forming a fluid barrier. Methods of manufacturing and bonding layers 10 together are disclosed in U.S. Patent Application Publication Nos. 2010/0042167, 2010/0042218 and 2010/0042215, which are incorporated in their entireties herein by reference.

Figure 10:
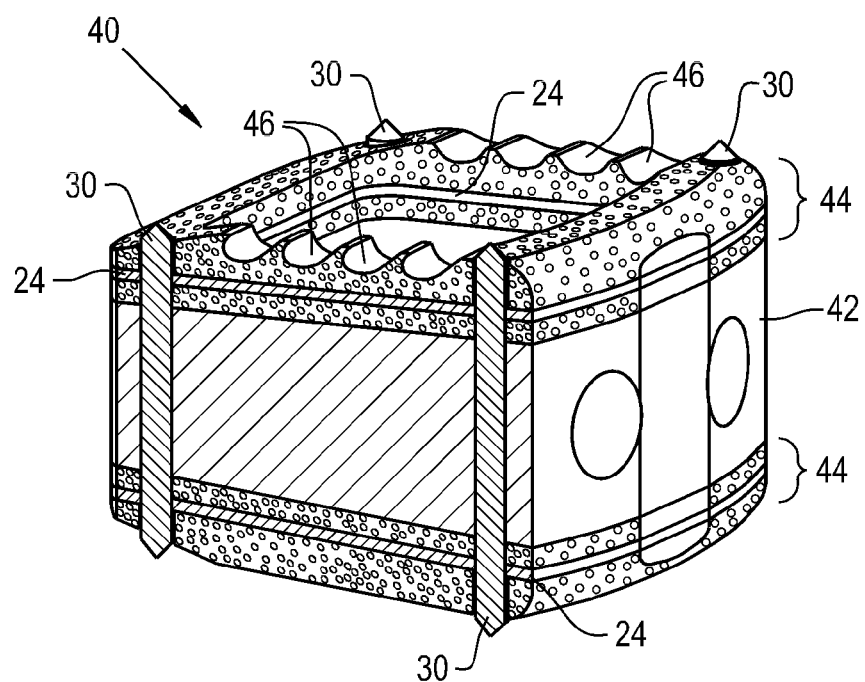
FIG. 10 is a sectioned perspective view of an additional embodiment of a medical implant according to the present invention.

Referring now to FIGS. 9 and 10, there is shown a medical implant 40 according to the present invention. Medical implant 40 generally includes a main body 42 and an insert 44 formed of a scaffold 20 coupled with main body 42.

Medical implant 40 is shown in FIGS. 9 and 10 as an implant for any of a number of, for example, spinal interbody devices used in different spinal surgical approaches, for example anterior cervical devices (cervical devices inserted from different orientations), lumbar and thoracic lumbar implants. The referenced cervical devices are typically inserted into the disc space of the cervical spine after the damaged or degenerated disc is removed. As shown in FIG. 10, medical implant 40 may also have grooves 46 formed in at least one, for example 2 surfaces. The grooves help to prevent back-out or expulsion of implant 40 after implantation. However, it also may be utilized in a number of other device applications, for example glenoid or acetabular implants (porous material may only be attached to one side of these devices), High Tibial Osteotomy (HTO) implants, and so on.

Medical implant 40 incorporates scaffold 20, as set forth more fully above, including a plurality of layers 10 bonded to each other and having a top surface 16 and a bottom surface 14. Each of layers 10 has a plurality of pores 12 extending from top surface 16 to bottom surface 18. A pore pattern of the pores 12 on top surface 16 of each of layers 10 is different than a pore pattern on bottom surface 18. Pores 12 of adjacent surfaces 16, 18 of at least three adjacent layers 10 have a substantially identical pore pattern over the course of at least three adjacent layers 10. Medical implant 30 may have 1 or more scaffolds 20, for example 2, 3, 4 or more scaffolds, which provide one or more roughened, porous surfaces on medical implant 40 for bone ingrowth. Each scaffold 20 of implant 30 is formed, for example of a biocompatible metal, such as titanium and titanium alloys, aluminum and aluminum alloys, and titanium-cobalt alloys. Scaffolds 20 of implant 40 may also be formed of a biocompatible polymeric material, for example a PAEK, such as PEEK, PEK, PEKK, or PEKEKK.

In the embodiment illustrated in FIGS. 9 and 10, main body 42 is positioned between two adjacent scaffolds 20, thereby providing, for example, a porous ingrowth surface on two opposing sides of implant 30 or, in the alternative, a porous ingrowth region 26 on one side and a poly-retention region 28 on an opposing side. In this case, for example, cephalad and caudal surfaces each have roughened surface for initial stability. The cephalad and caudal surfaces of implant 40 are thereby porous in nature to allow and encourage bone to grow into these surfaces, improving long-term fixation.

Main body 32 is formed, for example, of a biocompatible metal, plastic, polymeric material, or ceramic material. Suitable metals include titanium and titanium alloys, tantalum and tantalum alloys, cobalt chrome alloys, and stainless steel. Exemplary polymeric materials are, for example, a thermoplastic polymer that is non-resorbable and substantially inert, such as polyetheretherketone (PEEK). PEEK is especially suited for orthopaedic applications since it has a modulus of elasticity similar to that of bone, is resistant to compressive loading, has a high biocompatibility and biostability, and due to its radiolucency.

Figure 14:
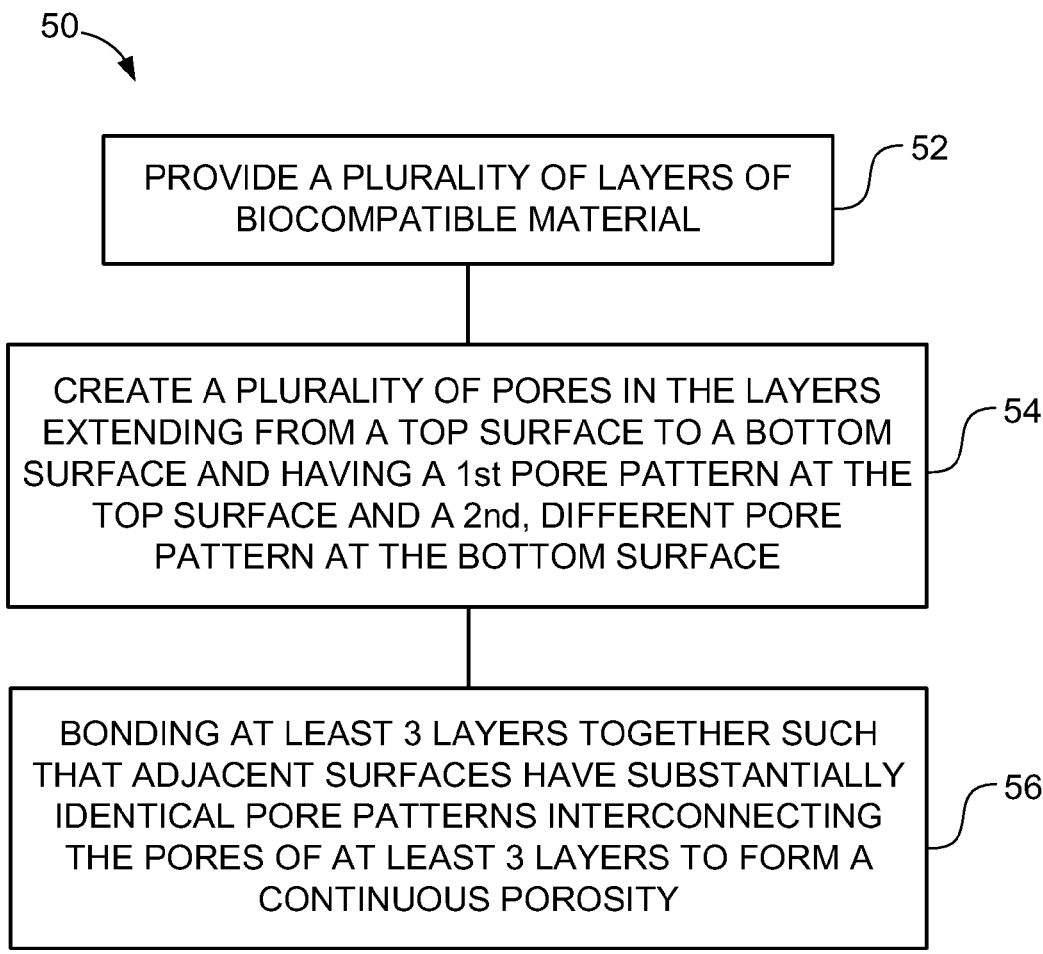
FIG. 14 is a flow chart of a method of manufacturing a scaffold for a medical implant according to the present invention.

Referring now to FIG. 14, the present invention further provides a method 50 for manufacturing a scaffold 20 for a medical implant according to the present invention. According to inventive method 50, a plurality of layers of a biocompatible material having a top surface and a bottom surface are provided, as indicated at step 52. According to the present invention, layers 10 formed of different materials may be utilized to form scaffold 20. For example, titanium layers and PEEK layers may be assembled to form three-dimensional scaffold 20.

A plurality of pores are created in the layers of biocompatible material such that at least some of the pores, for example all of the pores, extend from the top surface to the bottom surface and a pore pattern of the pores on the top surface is different than another pattern on the bottom surface, as indicated at step 54. According to one embodiment of the method for manufacturing a scaffold according to the present invention, pores are, for example, created in a respective layer from both sides, namely, from the top surface and from the bottom surface. Additional methods for creating pores 12 in layers 10 include, but are not limited to, chemical etching, photochemical etching, laser cutting, electron-beam machining, conventional machining, stamping, extrusion, rolling and knurling.

According to the present invention, different patterns are used to create pores on each side of a respective layer. Method 50 further provides for step 56, which includes bonding a plurality of the layers together to form a three dimensional scaffold such that adjacent top surfaces and bottom surfaces of respective adjacent layers have a substantially identical pore pattern aligning over the course of at least three adjacent layers. Bonding step 56 may be completed using diffusion bonding, sintering, laser welding, heat staking, thermal processing, ultrasonic welding, mechanical fastening, and/or adhesive bonding.

If scaffold 20 further includes a stiffening layer 24, all of the above-described layers of biocompatible material having the defined pore pattern may be first assembled together and bonded prior to bonding stiffening layer 24 thereto. Alternatively, stiffening layer 24 may be positioned at a predetermined position within the plurality of layers prior to bonding and thereafter bonded together in a single step. Regardless of which method of construction is utilized, if the material of scaffold 20 is a metal or a plurality of metals, for example titanium, then diffusion bonding can be used to bond the components of scaffold 20 together. Alternatively, sintering can be utilized to complete the bonding step. If the material of any of the components of the scaffold is a polymer, then heat staking can be used to bond the polymer components together. It is also possible to utilize a combination of diffusion bonding and heat staking, dependent upon the material(s) utilized, for example a combination of polymer materials and metal materials.

Figure 15:
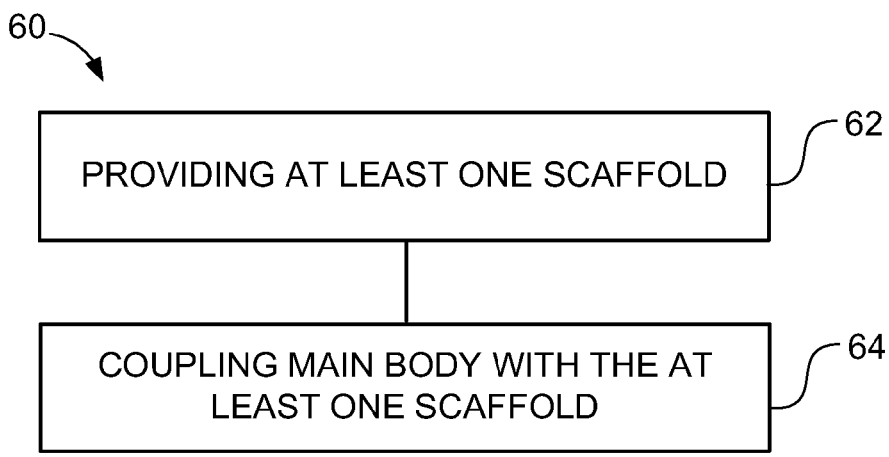
FIG. 15 is a method of manufacturing a medical implant according to the present invention.

Referring now to FIG. 15, there is shown a method 60 of forming a medical implant, which includes the step 62 of providing at least one scaffold 20, for example two scaffolds 20, which may be manufactured according to the method set forth above according to the present invention. Scaffold(s) 20 may include stiffening layer(s) 24, as set forth above. When two or more scaffolds 20 are utilized, method 60 provides for interconnection of the scaffolds 20 with a plurality of fixation devices, for example fixation pins, which are press fit between scaffolds 20 to securely affix each scaffold 20 into place. It is also feasible to provide a combination of alignment and fixation pins, each being press fit into scaffolds 20, connecting and aligning scaffolds 20 with each other.

A main body is then coupled 64 with scaffolds 20. Main body can be made from a variety of materials, including titanium and a cobalt/chromium alloy, and PEEK, among other materials. Coupling step 64 may be completed using diffusion bonding, mechanical fasteners, and injection molding. For example, scaffolds 20 are loaded into a mold and PEEK is injected (or alternatively heated and pressed) between scaffolds 20, filling the space therebetween to form a medical implant. Scaffolds 20 included herein not only have a porous ingrowth region, but also a porous polymer retention (poly-retention) region that allows the polymer, for example PEEK, to flow into and anchor the polymer, fusing the polymer to the scaffold 20 as the polymer cures. Stiffening layer 24 provide rigidity for the scaffold 20 during formation of the medical implant during the molding process. The process of injection molding employs a substantial amount of force to inject the polymer, therefore this stiffening layer helps the insert or scaffold to hold its form while the polymer is injected.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A three-dimensional scaffold for a medical implant, the scaffold comprising a plurality of layers bonded to each other and each said layer having a top surface and a bottom surface, each of said layers having a plurality of pores extending through said top surface to said bottom surface, each said layer having a first pore pattern of said plurality of pores at said top surface and a different, second pore pattern at said bottom surface, said first pore pattern and said second pore pattern partially overlapping within each said layer, wherein adjacent said surfaces of at least three adjacent said layers having a substantially identical pore pattern aligning to interconnect said plurality of pores of said at least three adjacent layers and form a continuous porosity through said at least three adjacent said layers.

2. The scaffold according to claim 1, each of said plurality of layers having at least one transition point where a geometry of said plurality of pores extending between said top surface and said bottom surface transitions from said first pore pattern to at least one said second pore pattern, said at least one transition point being at a position in a range between approximately 0.05 and 0.95 through a thickness of said respective layer.

3. The scaffold according to claim 2, wherein said at least one transition point is two transition points.

4. The scaffold according to claim 3, said thickness of each of said plurality of layers being in a range between approximately 0.0001 and 10 inches.

5. The scaffold according to claim 2, wherein different said pores of said plurality of layers have a plurality of different geometries.

6. The scaffold according to claim 1, wherein said plurality of layers of the scaffold include at least one interlocking feature allowing adjacent said layers to nest together.

7. The scaffold according to claim 6, wherein said interlocking feature is at least one undercut in at least one of said plurality of layers into which extends one of a strut of an adjacent one of said plurality of layers and a protrusion extending from said adjacent one of said plurality of layers.

8. A medical implant, comprising:
a main body; and
at least one scaffold coupled with said main body, said at least one scaffold including a plurality of layers bonded to each other, each said layer having a top surface and a bottom surface and a plurality of pores extending through said top surface to said bottom surface, each said layer having a first pore pattern of said plurality of pores at said top surface and a different, second pore pattern at said bottom surface, said first pore pattern and said second pore pattern partially overlapping within each said layer, wherein adjacent said surfaces of at least three adjacent said layers having a substantially identical pore pattern aligning to interconnect said plurality of pores of said at least three layers and form a continuous porosity through said at least three adjacent said layers.

9. The medical implant according to claim 8, wherein said main body is formed of a solid material.

10. The medical implant according to claim 9, wherein said solid material is one of an implantable polymer material and a solid metal.

11. The medical implant according to claim 10, wherein said implantable polymer material is polyetheretherketone (PEEK).

12. The medical implant according to claim 8, said at least one scaffold being formed of an implantable metal material.

13. The medical implant according to claim 8, wherein the medical implant is an implantable spinal device.

14. The medical implant according to claim 13, said at least one scaffold further comprising a plurality of anti-back out grooves.

15. The medical implant according to claim 14, said at least one scaffold further comprising a solid, stiffening layer, wherein said at least one scaffold is at least two scaffolds including at least one first scaffold and at least one second scaffold, said stiffening layer being positioned between said at least one first scaffold and said at least one second scaffold, sealing said at least one first scaffold from said at least one second scaffold.

16. The medical implant according to claim 15, said stiffening layer being formed from one of a biocompatible metal and a polymeric material.

17. The medical implant according to claim 16, wherein said stiffening layer has a pair of opposing surface, at least one of said opposing surfaces of said stiffening layer including a plurality of surface pores which do not extend through an entire thickness of said stiffening layer.

18. The medical implant according to claim 17, wherein said opposing surfaces of said stiffening layer include first surface and a second surface, each of said first surface and said second surface of said stiffening layer including a plurality of surface pores, said stiffening layer including a solid region between said surface pores of said opposing surfaces to prevent flow through from said first surface of said stiffening layer to said second surface of said stiffening layer.

19. The medical implant according to claim 18, further comprising at least one alignment pin for holding said stiffening layer in position.

20. The medical implant according to claim 8, wherein said plurality of layers is at least four layers and one layer of said at least four layers is configured such that a plurality of solid regions of said one layer abut said plurality of pores of an adjacent one of said plurality of layers to prevent flow through between said one layer and an adjacent layer of said at least four layers.

21. A method of manufacturing a scaffold for a medical implant, the method comprising the steps of:
providing a plurality of layers of a biocompatible material having a top surface and a bottom surface;
creating a plurality of pores in said plurality of layers of biocompatible material such that each of said layers has a plurality of pores extending through said top surface to said bottom surface, a first pore pattern of said plurality of pores at said top surface of each of said layers being different than a second pore pattern of said bottom surface of each of said layers, and said first pore pattern and said second pore pattern partially overlap within each said layer; and
bonding said plurality of layers together such that adjacent said surfaces of at least three adjacent said layers have a substantially identical pore pattern aligning to interconnect said plurality of pores of said at least three layers forming a continuous porosity through said at least three adjacent said layers.

\* \* \* \* \*